(12) United States Patent
Kugel et al.

(10) Patent No.: US 6,176,863 B1
(45) Date of Patent: *Jan. 23, 2001

(54) HERNIA MESH PATCH WITH I-SHAPED FILAMENT

(75) Inventors: Robert D. Kugel, Olympia, WA (US); J. Douglas Inman, Arlingtion; Keith D. Biggers, Southlake, both of TX (US)

(73) Assignee: Bard ASDI Inc., Murray Hill, NJ (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/275,587

(22) Filed: Mar. 24, 1999

Related U.S. Application Data

(63) Continuation-in-part of application No. 09/006,653, filed on Jan. 14, 1998, now Pat. No. 5,916,225, which is a continuation of application No. 08/955,108, filed on Nov. 26, 1996, now Pat. No. 5,769,864, which is a continuation-in-part of application No. 08/315,249, filed on Sep. 29, 1994, now Pat. No. 5,634,931
(60) Provisional application No. 60/095,694, filed on Aug. 7, 1998.

(51) Int. Cl.[7] .................................................. A61B 17/04
(52) U.S. Cl. ................................ 606/151; 602/44; 602/58
(58) Field of Search ..................................... 606/151, 213, 606/214, 215, 110, 113; 602/44, 58

(56) References Cited

U.S. PATENT DOCUMENTS

| | | | |
|---|---|---|---|
| 2,671,444 | 3/1954 | Pease, Jr. | 606/151 |
| 3,054,406 | 9/1962 | Usher | 606/151 |
| 4,007,743 | 2/1977 | Blake . | |
| 4,347,847 | 9/1982 | Usher | 606/151 |
| 4,452,245 | 6/1984 | Usher | 606/151 |
| 4,561,434 | 12/1985 | Taylor . | |

(List continued on next page.)

FOREIGN PATENT DOCUMENTS

| | | |
|---|---|---|
| 2114282 | 7/1994 | (CA) . |
| 0 362 113 | 4/1990 | (EP) . |
| 0 474 887 | 10/1991 | (EP) . |
| 676 285 | 7/1979 | (SU) . |
| 782 814 | 11/1980 | (SU) . |
| WO 90/14796 | 12/1990 | (WO) . |
| WO 93/17635 | 9/1993 | (WO) . |
| WO 94/27535 | 12/1994 | (WO) . |
| WO 97/22310 | 6/1997 | (WO) . |

OTHER PUBLICATIONS

Gregory L. Brown, M.D. et al., "Comparison of Prosthetic Materials for Abdominal Wall Reconstruction in the Presence of Contamination and Infection", Annals of Surgery, Jun. 1985, vol. 201, pp. 705–711.

(List continued on next page.)

*Primary Examiner*—Gary Jackson
(74) *Attorney, Agent, or Firm*—Wolf, Greenfield & Sacks, P.C.

(57) ABSTRACT

A hernia patch has a first layer of inert synthetic mesh material selectively sized and shaped to extend across and beyond a hernia. A second layer of inert synthetic mesh material overlies the first layer to create a generally planar configuration for the patch. The first and second layers are joined together by a seam that defines a periphery of a pouch between the layers. One of the layers has a border that extends beyond the seam and has a free outer edge. A plurality of border slits extend from the outer edge through the border substantially to the seam. Access slits are formed between the layers to allow insertion of a surgeon's finger into the pouch. The pouch allows the surgeon to deform the planar configuration of the patch to facilitate insertion of the patch into the patient and to position the patch across the hernia. A resilient monofilament I-shaped spring is located within the pouch at the seam for urging the patch to conform to the generally planar configuration across the hernia as the surgeon withdraws his or her finger.

11 Claims, 2 Drawing Sheets

U.S. PATENT DOCUMENTS

| | | | |
|---|---|---|---|
| 4,633,873 | 1/1987 | Dumican et al. | 606/151 |
| 4,655,221 | 4/1987 | Devereux | 606/151 |
| 4,693,720 | 9/1987 | Sharnberg et al. | 606/151 |
| 4,710,192 | 12/1987 | Liotta et al. . | |
| 4,769,038 | 9/1988 | Bendavid . | |
| 4,796,603 | 1/1989 | Dahlke . | |
| 4,854,316 | 8/1989 | Davis . | |
| 4,865,026 | 9/1989 | Barrett . | |
| 4,955,907 | 9/1990 | Ledergerber . | |
| 5,006,106 | 4/1991 | Angelchik . | |
| 5,059,205 | 10/1991 | El-Nounou et al. . | |
| 5,116,357 | 5/1992 | Eberbach | 606/151 |
| 5,122,155 | 6/1992 | Eberbach | 606/151 |
| 5,141,515 | 8/1992 | Eberbach | 606/151 |
| 5,147,374 | 9/1992 | Fernandez | 606/151 |
| 5,147,387 | 9/1992 | Jansen . | |
| 5,176,692 | 1/1993 | Wilk et al. . | |
| 5,192,301 | 3/1993 | Kamiya et al. . | |
| 5,195,542 | 3/1993 | Gazielly et al. . | |
| 5,201,745 | 4/1993 | Tayot et al. . | |
| 5,254,133 | 10/1993 | Seid . | |
| 5,258,000 | 11/1993 | Gianturco . | |
| 5,290,217 | 3/1994 | Campos . | |
| 5,334,217 | 8/1994 | Das . | |
| 5,350,399 | 9/1994 | Erlebacher et al. | 606/151 |
| 5,356,432 | 10/1994 | Rutkow et al. . | |
| 5,366,460 | 11/1994 | Eberbach | 606/151 |
| 5,368,602 | 11/1994 | de la Torre | 606/151 |
| 5,370,650 | 12/1994 | Tovey et al. . | |
| 5,397,331 | 3/1995 | Himpens et al. . | |
| 5,425,744 | 6/1995 | Fagan et al. . | |
| 5,433,996 | 7/1995 | Kranzler et al. . | |
| 5,451,235 | 9/1995 | Lock et al. . | |
| 5,456,720 | 10/1995 | Schultz et al. . | |
| 5,507,811 | 4/1996 | Koike et al. . | |
| 5,593,441 | 1/1997 | Lichtenstein et al. . | |
| 5,614,284 | 3/1997 | Kranzler et al. . | |
| 5,695,525 | 12/1997 | Mulhauser et al. . | |
| 5,702,416 | 12/1997 | Kieturakis et al. . | |
| 5,716,408 | 2/1998 | Eldridge et al. . | |
| 5,743,917 | 4/1998 | Saxon . | |
| 5,824,082 | 10/1998 | Brown . | |
| 5,836,961 | 11/1998 | Kieturakis et al. . | |
| 5,879,366 | 3/1999 | Shaw et al. | 606/151 |
| 5,919,232 | 7/1999 | Chaffringeon et al. | 606/151 |
| 5,922,026 | 7/1999 | Chin . | |
| 5,954,767 | 9/1999 | Pajotin et al. . | |

OTHER PUBLICATIONS

Scott D. Jenkins, M.D. et al., "A Comparison of Prosthetic Materials Used to Repair Abdominal Wall Defects", Surgery, Aug. 1983, vol. 94, No. 2, pp. 292–398.

"Prevention of Postsurgical Adhesions by Interceed (TC7)", Fertility and Sterility, Jun. 1989, vol. 51, No. 6, pp. 933–938.

Hernando Cordona M.D., "Prosthokeratoplasty", 1983, Cornea, vol. 2, No. 3, 1983, pp. 179–183.

Alonzo P. Walker, M.D., et al., "Double–Layer Prostheses for Repair of Abdominal Wall Defects in a Rabbit Model", pp. 32–37, Journal of Surgical Research, vol. 55, No. No. 1, Jul. 1993.

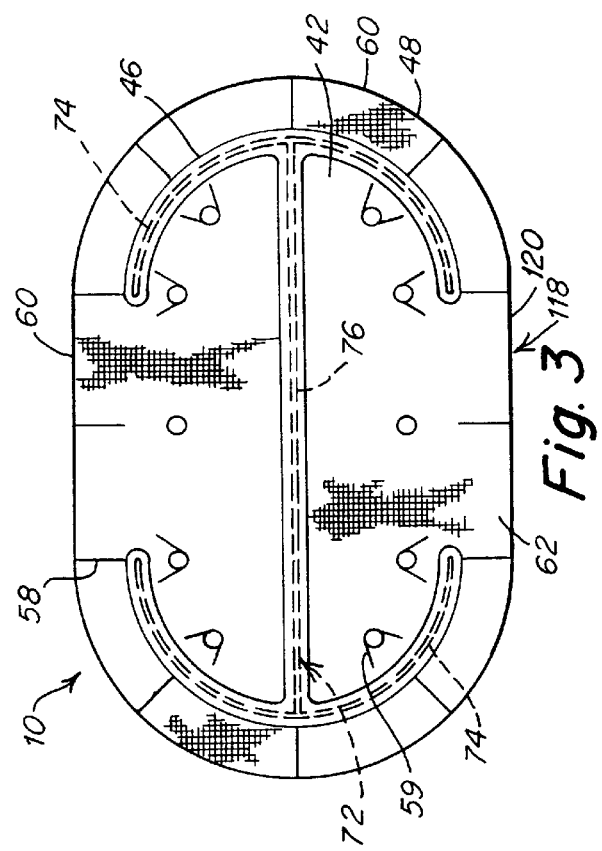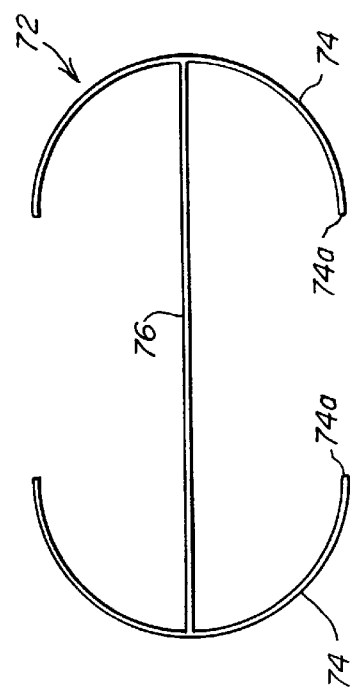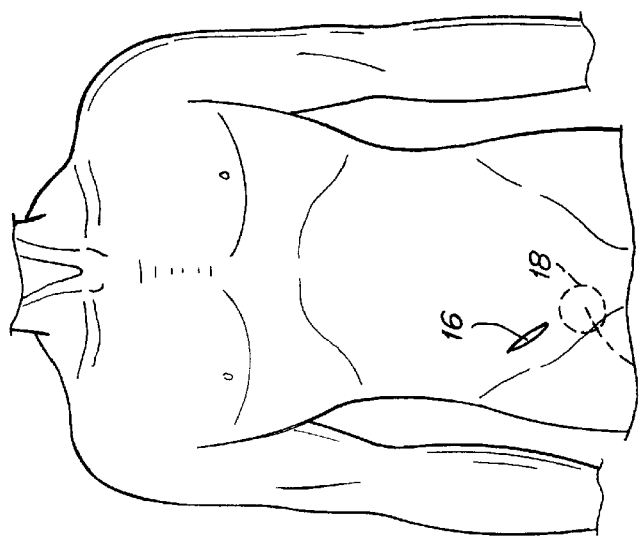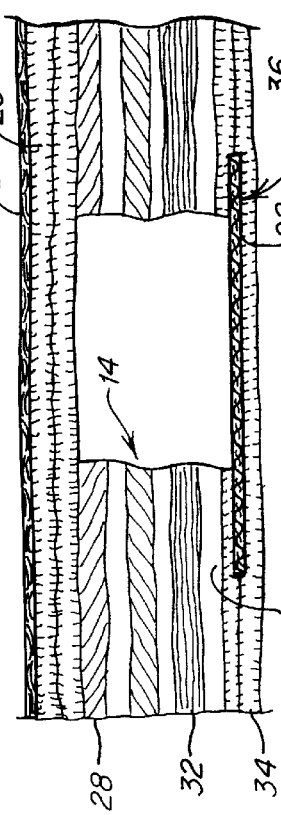

HERNIA MESH PATCH WITH I-SHAPED FILAMENT

CROSS-REFERENCE TO RELATED APPLICATION

This application claims the benefit of provisional application Ser. No. 60/095,694, filed Aug. 7, 1998, and is a continuation-in-part of application Ser. No. 09/006,653, filed Jan. 14, 1998, now U.S. Pat. No. 5,916,225, which was a continuation of application No. 08/755,108, Nov. 22, 1996, Pat. No. 5,769,864, which is a continuation-in-part of application No. 08/315,249, Sep. 29, 1994, Pat. No. 5,634,931.

TECHNICAL FIELD

The present invention generally relates to a surgically implantable patch for use in repairing a hernia or other wound. More particularly, the present invention relates to a hernia repair patch having an I-shaped filament to maintain the patch in a planar configuration.

BACKGROUND OF THE INVENTION

Surgically implantable mesh patches for the repair of inguinal and other abdominal wall hernias, which are intended for permanent placement within a patient's body space, have been provided and used previously. Tension free surgical repairs of hernias have been developed using synthetic mesh materials to bridge and to patch hernia defects. These repairs resulted in both a decrease in the recurrence rate as well as a decrease in the amount of a patient's post operative discomfort. Patients undergoing these more advanced procedures were able and are able to resume their normal activities sooner.

Some of these earlier techniques are somewhat complicated. Several use a plug or a locating member to fit within the hernia defect itself. Many of the earlier techniques were designed specifically for use in laparoscopic repair of hernias. Moreover, many of the prior inventions required suturing the patch to the patient's body tissue. Although these medical advances are acknowledged for their usefulness and success, there remained a need or needs for more improvements in the surgical repair of hernias.

DISCLOSURE OF INVENTION

A hernia mesh patch for use in the surgical repair of a patient's inguinal, or other abdominal wall hernias, is disclosed for permanent placement within a patient's body space. The hernia mesh patch of the invention has a top layer and a bottom layer of an inert, synthetic mesh, preferably polypropylene mesh, secured to each other with a seam. The seam is preferably formed by an ultrasonic weld that surrounds a stiffener or spring.

To serve a spring function, an implantable inert monofilament fiber, arranged in a configuration approximating an "I" shape, is welded between a top layer and a bottom layer of the hernia mesh patch to keep the hernia mesh patch expanded under tension in a planar configuration. The seam runs lengthwise over the patches and around each end, approximating an "I" shape. A border on at least one of the layers extends outward past the seam. The border preferably has slits that define tabs that fill uneven voids in the patient's tissue and fit more tightly with a patient's tissues.

Without the need for general anesthesia, nor expensive laparoscopic instrumentation, a surgeon repairs an inguinal hernia by making a small incision in the patient. The incision is approximately three centimeters long, is arranged obliquely, and is approximately two to three centimeters above the internal ring location of the inguinal hernia. Operating through the small incision, the surgeon uses a muscle splitting technique to perform a dissection deep into the patient's properitoneal space. The dissection creates a pocket in the space into which the hernia mesh patch may be inserted.

Thereafter, the surgeon uses his or her fingers to readily fold and compact the hernia mesh patch. The surgeon then directs the patch through the incision and into the patient's properitoneal space. The patch may then unfold and expand into its planar configuration to create a trampoline effect. The surgeon may place a finger partially through an opening between the top and bottom layers of the hernia mesh patch to conveniently and accurately move the hernia mesh patch into position to cover the defect in the patient's thick reinforcing lining of the patient's abdominal cavity. Thereafter, the surgeon withdraws his or her finger and secures the incision with stitches.

Soon after surgery, the patient's body reacts to the mesh of the hernia mesh patch. In a short time, the mesh becomes stuck, thereby keeping the hernia mesh patch in place. Thereafter, the patient's scar tissue grows into the mesh over a period of time, typically between thirty and sixty days, to permanently fix the hernia mesh patch in its intended position over the area where the hernia was located.

Small holes are cut through both layers of the mesh to increase friction and to minimize the sliding or migration of the hernia mesh patch once the patch is positioned. In one embodiment, spaced darts are attached to the material in one of the layers to serve as anchors for engaging the patient's tissue.

BRIEF DESCRIPTION OF DRAWINGS

FIG. 1 is a schematic partial front view of a patient's body, which indicates repair of an inguinal hernia.

FIG. 2 is a schematic partial diagrammatic cross-sectional view of a patient's abdominal wall layers showing an inguinal or other abdominal wall hernia, with a hernia repair mesh patch positioned in the properitoneal created space.

FIG. 3 is a top view of a preferred embodiment of the surgically implantable hernia repair mesh patch.

FIG. 4 is a top view of the resilient monofilament spring of the invention.

BEST MODE FOR CARRYING OUT THE INVENTION

Figure 5:
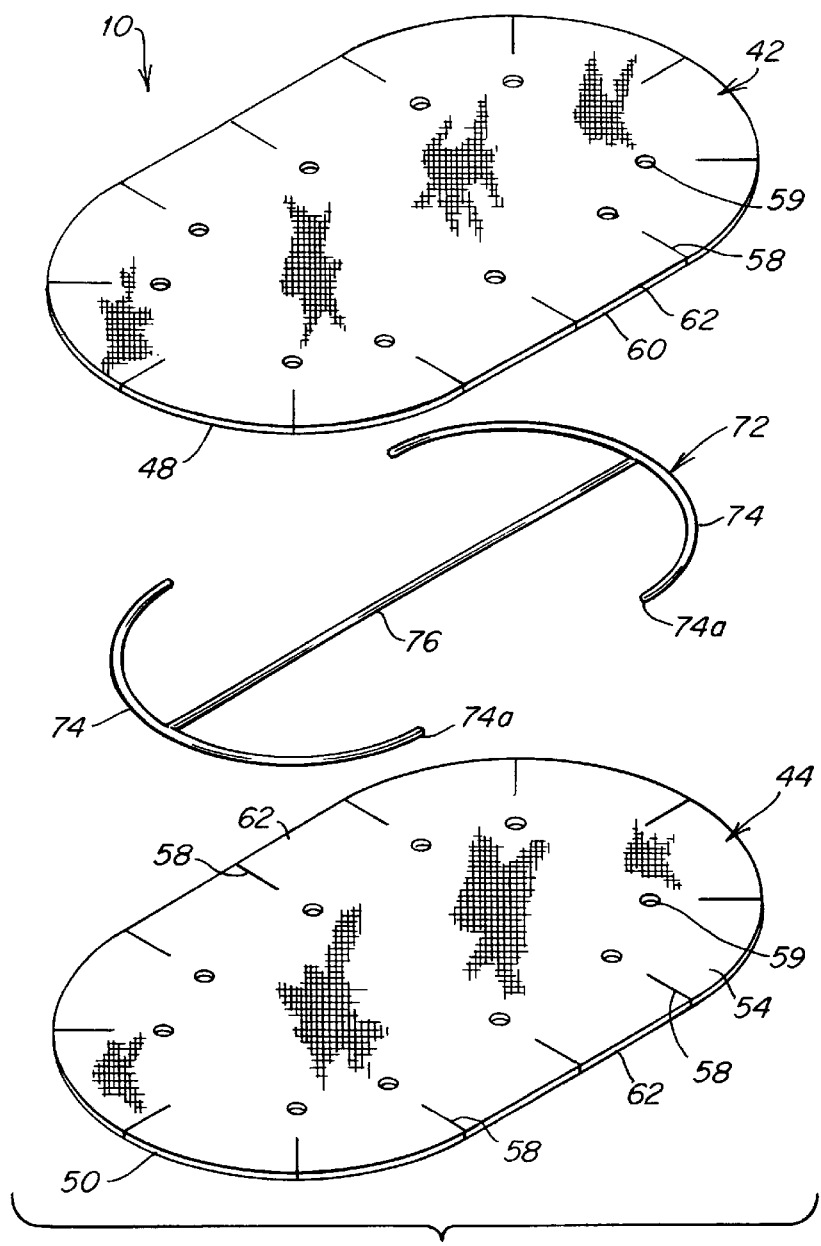
FIG. 5 is an exploded view of the surgically implantable hernia repair mesh patch shown in FIGS. 2 and 3 that shows the two layers of the mesh and also the resilient monofilament I-shaped spring.

The hernia mesh patch 10, illustrated in the drawings, is surgically permanently implantable within a patient's body space to adequately cover, correct, prevent and repair any inguinal or other abdominal wall hernias 14 or other types of hernias or wounds. The surgeon has the objective of making a sutureless repair, by first cutting an approximately three centimeter incision 16. The incision 16 is obliquely positioned approximately two to three centimeters above the location described as the internal ring 18, where an inguinal hernia 14 has occurred, as shown in FIG. 1. The surgeon then works through incision 16 and uses a muscle splitting technique to dissect deeply into the patient's properitoneal space 20. The surgeon enters slightly superior and posterior of the patient's hernia defect 14. The surgeon then creates a pocket 22 in the patient's properitoneal space 20, into which the hernia mesh patch 10 is inserted, as shown in FIG. 2.

The surgeon dissects deeply into the patient's properitoneal space 20, as indicated in FIG. 2, with a sharp instrument to make the incision or wound 16 through the patient's skin 24, the subcutaneous fatty tissues 26, and the external oblique fascia 28, which has been cut parallel with its fibers a short distance. The surgeon then incises the transversalis fascia 32 to create an entrance into the properitoneal space 20, above the peritoneum 34 at a location superior to the hernia 14. In so doing, the surgeon identifies and frees up the hernia sac and creates a pocket 22 in the properitoneal space 20. Space 20 underlies the area referred to as Hesselbach's triangle, in reference to both indirect and direct hernias. The surgeon's placement of hernia mesh patch 10 protects the entire inguinal floor. Therefore, the placement of the patch not only repairs or corrects a single small hernia, but also protects against future hernias through other potentially weakened areas. In a similar way, a hernia mesh patch 10 is sandwiched between a hernia 14 or defect and the inner lining 34 or peritoneum of the abdominal cavity 36. The hernia mesh patch 10 is used to underlay a femoral canal area (not shown) through which femoral hernias occasionally occur. Wherever used, the hernia mesh patch 10 serves as a basis for tension-free surgical repair of a hernia, as it is used to patch and to bridge the hernia 14. The surgeon may then use his or her fingers to fold and compact the hernia mesh patch 10 and insert the patch down through the incision 16 into properitoneal space 20. Thereafter, the surgeon expands, moves, and directs the hernia mesh patch 10 into position in the pocket 20 within the properitoneal space 20 to bridge the hernia 14.

Figure 6:
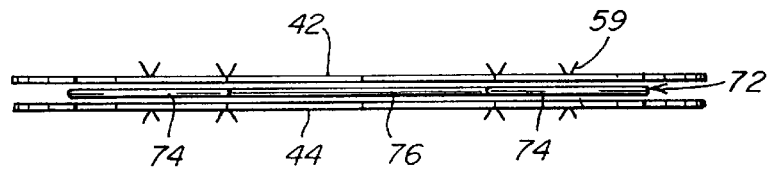
FIG. 6 is a transverse cross sectional view of the center of the preferred surgically implantable hernia repair mesh patch, illustrated in FIGS. 2, 3 and 5, with the top and bottom layers shown slightly separated for illustrative purposes.

One embodiment of hernia mesh patch 10 is illustrated in FIGS. 2 through 6, which is particularly designed for the repair of an inguinal hernia 10 but also can be used for other abdominal wall hernias. Hernia mesh patch 10 is composed of two similarly shaped pieces of an inert synthetic mesh material or a top layer 42 and a bottom layer 44. The sizes of layers 42, 44 may be the same. Top layer 42 and bottom layer 44 are preferably constructed of a polypropylene material. The mesh material is preferably formed from a monofilament material that is resistant to infection, and that has been used safely in many hernia operations, in previous ways and in previous embodiments. Preferably, the two layers 42, 44 are made in a circle, loop, ovoid, or oval shape or a partial circle, loop, ovoid, or oval shape. Layers 42, 44, are secured to each other with a seam 46. Seam 46 is preferably formed by ultrasonic welding, but other types may work also. Seam 46 is approximately one centimeter in from outer edge 48 of top layer 42 and outer edge 50 of bottom layer 44. The outer one centimeter of mesh material of the bottom layer 44 is left free to serve as a border or apron 54 to fill uneven voids in the patient's tissue.

When the hernia mesh patch 10 has been placed in a patient's properitoneal space, the free border 54 serves to frictionally keep the patch 10 in the appropriate hernia repair position. Inside of the seam 46, like-sized darts 59 (FIG. 3) are positioned in the top and bottom mesh layers 42, 44. Preferably aligned one above the other, the presence of darts 59 help initially to frictionally keep the hernia mesh patch 10 in place. Thereafter, the patient's scar tissues grow in and around darts 59 to continue to keep the hernia mesh patch in position. The outer one centimeter of the mesh materials of layers 42, 44 are cut to form slits 58, which radially or diagonally create scalloped or fringed edges 60. Fringed edges 60 define tab portions 62 on the outer one centimeter of mesh materials on the top and bottom mesh layers 42, 44.

A generally I-shaped spring 72 is positioned between the top layer 42 and the bottom layer 44. Seam 46 has the same shape as spring 72 and closely surrounds the I-shaped spring 72. I-shaped spring 72 keeps patch 10 fully extended in a planar arrangement, as shown in FIG. 2. Spring 72 is made of a synthetic material, such as nylon, polypropylene, or polyester.

The resilient spring 72 is preferably constructed of a monofilament fiber. Spring 72 has two curved cross-members 74 located at each end of a longitudinal member 76. Each cross-member 74 curves toward the other, forming a semi-circle. The ends 74a of one cross-member 74 are spaced longitudinally from ends 74a of the other cross-member. The cross-members 74 of spring 72 are located outward of darts 59 and slightly inward of outer edge 60 of layer 42, as shown in FIG. 3. Seam 46 surrounds spring 72. Therefore, a portion of seam 46 is slightly inward of the cross-members 74 of spring 72 and a portion of seam 46 is also located slightly outward of the cross-members 74 of spring 72. Additionally, seam 46 runs the length of longitudinal member 76.

Seam 46 is located inward from outer edge 60 of layer 42 and slightly inward of border slits 58. Seam 46 and ends 74a define a pocket or pouch 118 between layers 42, 44. Access openings 120 on each side serve as access to pouch 118. Cross-members 74 of spring 72 are located at the periphery of pouch 118. Spring 72 urges patch 10 to a flat configuration. This configuration may be deformed during the insertion and placement of patch 10. Dart tabs 59 protrude from the surface of layer 42. Dart tabs 59 frictionally engage tissue when patch 10 is implanted within a patient to hold patch 10 in place without the need for sutures.

In use, a surgeon uses both sharp and blunt instruments to create pocket 22 in a patient's properitoneal space 20. The surgeon selects the type and size embodiment of the hernia mesh patch 10 best suited to be used in the repair of the patient's defect or hernia 14. The selected hernia mesh patch 10 is folded and further compacted, as may be necessary, by the surgeon so that the selected patch 10 may be conveniently inserted through the wound or incision 16 and down into the properitoneal space 20.

Referring to FIG. 3, the hernia mesh patch 10 is allowed to expand under the force of the spring 72 within space 20. Thereafter, the surgeon uses his or her finger to continue any further expansion of patch 10 that may be necessary. The surgeon then inserts a finger through the opening 120 along the center of the long edge of patch 10. The hernia mesh patch 10 is inserted through the properitoneal space to the pocket 22. After withdrawal of the surgeon's finger, the surgeon completes the repair surgery by closing the wound or incision with stitches using the remote incision 16, as illustrated in FIG. 1.

In the repair of other hernias, and especially those that are large, a direct incision is made. After the placement of a large hernia mesh patch, the surgeon may use limited sutures to keep the larger hernia mesh patch in place. Generally, most of the embodiments of this hernia mesh patch 10 are positioned, and so remain, without the use of sutures.

The hernia mesh patches of the invention are simple to manufacture and to use with the surgical method of insertion. Patches 10 adequately underlay a hernia 14 or defect 14, with a minimum of two centimeters of a surrounding underlay about the circumference of the hernia 14. The patch 10 of the invention has sufficient rigidity and engages a patient's tissue with sufficient friction to eliminate or minimize sliding or migration. The repair of a patient's hernia 14 is achieved through a smaller wound or incision 16, with less surgical tension, less post-operative patient discomfort, shorter operation time, and at a potentially lower cost to the patient. The patient's post-operative discomfort is decreased, and risk of any recurrence is likewise decreased.

While the invention has been shown in several embodiments, it should be apparent that it is not limited to those embodiments but is susceptible to various changes without departing from the scope of the invention.

We claim:

1. A tissue aperture repair patch for implanting within a patient, comprising:
    at least one layer of inert synthetic mesh material sized and shaped to extend across and beyond a tissue aperture in a patient; and
    a resilient generally I-shaped support member for urging the layer to assume a flat configuration, said support member carried by the layer so as to remain implanted with the layer in the patient.

2. The patch according to claim 1 wherein the layer of inert synthetic mesh material has a periphery extending beyond an end of said resilient I-shaped support member that defines a border having a free outer edge to fill uneven voids in a patient's tissue.

3. The patch according to claim 1 wherein the support member is comprised of monofilament fiber.

4. The patch according to claim 1, further comprising:
    a first layer and a second layer;
    an opening on an edge of said patch for insertion of a finger between said layers to position said patch across the hernia.

5. The patch according to claim 1 wherein:
    said I-shaped support member is a monofilament fiber having a longitudinal member and a cross-member located on each end of the longitudinal member, the cross-member being transverse to the longitudinal member.

6. The patch according to claim 1 wherein:
    said I-shaped support member is a monofilament fiber having a longitudinal member and a cross-member located on each end of the longitudinal member, the cross-members being transverse to the longitudinal member and curved towards each other.

7. The patch according to claim 1 wherein:
    said I-shaped support member is a monofilament fiber having a longitudinal member and a cross-member located on each end of the longitudinal member, the cross-members being transverse to the longitudinal member, said I-shaped support member surrounded by an ultrasonic seam.

8. A tissue aperture repair patch for implanting in a patient, comprising:
    a first layer of inert synthetic mesh material sized and shaped to extend across and beyond a tissue aperture in a patient;
    a second layer of inert synthetic mesh material secured to the first layer to create a pouch between the first and second layers;
    an opening in an edge of said layers, providing access to an interior of the pouch to position the patch across the tissue aperture; and
    a resilient support member having a longitudinal member and a cross-member located on each end of the longitudinal member, said cross-members adjacent a periphery of the pouch for tending to cause both of the layers to assume a planar configuration, the support member being carried by the layers so as to remain implanted with the layers in the patient.

9. The patch according to claim 8, wherein:
    the support member is a monofilament fiber located within the pouch.

10. A tissue aperture repair patch for implanting in a patient, comprising:
    a first layer of inert synthetic mesh material sized and shaped to extend across and beyond a tissue aperture in a patient;
    a second layer of inert synthetic mesh material secured to the first layer to create a pouch between the first and second layers;
    a resilient support member having a longitudinal member, a first cross-member located on a first end of the longitudinal member and a second cross-member located on a second end of the longitudinal member, said cross-members being adjacent a periphery of the pouch for causing both of the layers to conform to a generally planar configuration, the support member being carried by the layers so as to remain implanted with the layers in the patient; and
    an opening in an edge of said layers for insertion of a finger into the pouch to position the patch across the tissue aperture, said opening between an end of said first cross-member and an end of said second cross-member.

11. A tissue aperture repair patch for implanting in a patient, comprising:
    a first layer of inert synthetic mesh material sized and shaped to extend across and beyond a tissue aperture in a patient;
    a second layer of inert synthetic mesh material secured to the first layer to create a pouch between the first and second layers;
    a resilient generally I-shaped support member having a longitudinal member and a first cross-member located on a first end of the longitudinal member and a second cross-member located on a second end of the longitudinal member, said cross-members adjacent a periphery of the pouch for creating tension in both of the layers, the support member being carried by the layers so as to remain implanted with the layers in the patient; and
    an opening in an edge of said layers for insertion of a finger into the pouch to position the patch across the tissue aperture, said opening between an end of said first cross-member and an end of said second cross-member.

* * * * *